United States Patent [19]

Reznichenko et al.

[11] Patent Number: 5,094,523
[45] Date of Patent: Mar. 10, 1992

[54] BIDIRECTIONAL LIGHT STEERING APPARATUS

[75] Inventors: Yakov Reznichenko, Brookline; Michael T. Milbocker, Boston, both of Mass.

[73] Assignee: Eye Research Institute of Retina Foundation, Boston, Mass.

[21] Appl. No.: 522,376

[22] Filed: May 11, 1990

[51] Int. Cl.⁵ .............................................. A61B 3/10
[52] U.S. Cl. .................................... 351/221; 359/861
[58] Field of Search ............... 351/206, 208, 211, 221; 350/169, 622

[56] References Cited

U.S. PATENT DOCUMENTS

4,768,873  9/1988  Webb .................................. 351/221
4,856,891  8/1989  Pflibsen et al. ...................... 351/206

Primary Examiner—Paul M. Dzierzynski
Attorney, Agent, or Firm—Lahive & Cockfield

[57] ABSTRACT

An optical steering assembly includes first and second steering elements, such as orthogonally-oriented galvanometer mirrors, scanners or acousto-optical cells, for redirecting light in both forward and return optical paths without crosstalk or mixing. Input light traveling in the first direction is directed from the first side of the first element to the first side of the second element, undergoing two orthogonal steering deflections to a redirected output path. Return light along the same or a closely adjacent path is directed at the second side of one element, where an optical relay system translates it to the second side of the other element. The return light thus strikes the opposite sides of the same elements as the input light, and undergoes corresponding steering corrections while maintaining complete beam separation. The assembly is especially useful in instruments where low light levels, scan distortion, or crosstalk would otherwise limit performance. A two dimensional fundus tracker employs one such assembly as an objective steering system for all illumination, and two further assemblies for positioning tracking beams directed into the objective steering system.

20 Claims, 5 Drawing Sheets

BIDIRECTIONAL LIGHT STEERING APPARATUS

BACKGROUND OF INVENTION

The present invention relates to optical assemblies for steering or redirecting light wherein light travels in forward and reverse directions through the steering assembly. One example of such a device is a scanning ophthalmic microscope, wherein light is directed along an input path at x- and y- axis steering mirrors before being focused at a target within the eye, and light reflected from the target is imaged back along substantially the same input path to the x- and y- axis steering mirrors before it is split off and directed to a photodetector or imaging device.

More generally, a clinical system may require that one or more input light beams and one or more observation beams all be steered together. In such a system, the input light may be a diagnostic illumination beam such as the infrared beam of a laser Doppler instrument, or a treatment beam such as a thin or point-focused surgical laser beam, directed along the steered path. Direct illumination for imaging light may also be provided independently of the mirror, for example, by flooding the eye with sufficient light to view the surgical field. The observation beam or beams may include return light which is focused to a visual image, transformed to a localized electrically-converted tracking image signal, converted to a tissue reflectance value for laser intensity control, or processed in some other way. For such an instrument, it is desirable that the treatment light and the collected return light both pass through steering mirrors to vary the field of treatment or observation, respectively.

One instrument of this type is described in U.S. Pat. No. 4,856,891 owned by the assignee of the present patent application. That patent discloses an ophthalmic instrument which steers a narrow diagnostic or treatment light beam, and receives a return image through a common steering system. The advantage of such a bidirectional steering system is that by moving the steering mirror or mirrors in a manner to stabilize the position of the return image, the input light path followed by the diagnostic or treatment beam is automatically maintained in a stable location on the eye fundus and that location bears a fixed spatial relation to the imaged area. However, when applying such a system to a target object on the fundus of the eye, scattering of the relatively intense input light in the steering assembly can add substantial noise to the extremely weak return signal. In addition, when it is desired to maintain a steering mirror and one or more stops in positions confocal with the observed field or with the pupil of the eye, precision is required in locating or aligning the beam with respect to these elements. This complicates the problem of maintaining different light systems sufficiently distinct, and further compounds the noise or crosstalk problems. When one of the mirrors is a scanning polygon and its faces undergo both translational and rotational motion, problems of varying optical path length, shifting mirror position and changing mirror incidence angle further complicate the task of forming a high quality image or maintaining several optical paths in registration with each other.

Accordingly, it is desired to provide a bidirectional optical steering system which corrects one or more of these shortcomings.

SUMMARY OF INVENTION

These and other problems of the prior art are overcome in a bidirectional steering system comprising a pair of moving light-directing elements each having first and second sides, wherein light traveling in one direction is redirected from the first sides of both elements, and light traveling in the other direction is redirected from the second sides of both elements preferably, the elements are relatively thin planar mirrors which each steer the light about one of two perpendicular axes. The first and second sides each sweep out virtually identical purely pivotal scanning motion, free of translation, to provide a wide field scan which is not occluded by system pupils. The first and second directions may be used for illumination and imaging light for a common objective lens assembly, thus allowing highly efficient and jitter-free imaging while providing effective I/O beam separation for such difficult applications as simultaneously treating and imaging the fundus of the eye.

In a preferred embodiment, a telecentric relay system translates one optical path from the second side of one element to the second side of the other element. The two elements are adjacent, placed such that their inside faces determine one optical path and their outside faces the other. Different embodiments may employ a polygonal scanning drum or possibly an arrangement of one or more acousto-optic modulators to redirect the light paths. Preferably the telecentric relay between faces of steering elements is effected by curved mirrors. Systems incorporating the invention include fundus tracking instruments and devices such as microscope, Doppler measurement and laser surgery devices. Other applications involving bidirectional steering with a low level of observation light may include instruments for surveying, surveillance or optical communications.

BRIEF DESCRIPTION OF THE DRAWINGS

These and other properties of the invention will be understood with reference to the drawings of illustrative embodiments, wherein.

DETAILED DESCRIPTION

Figure 1:
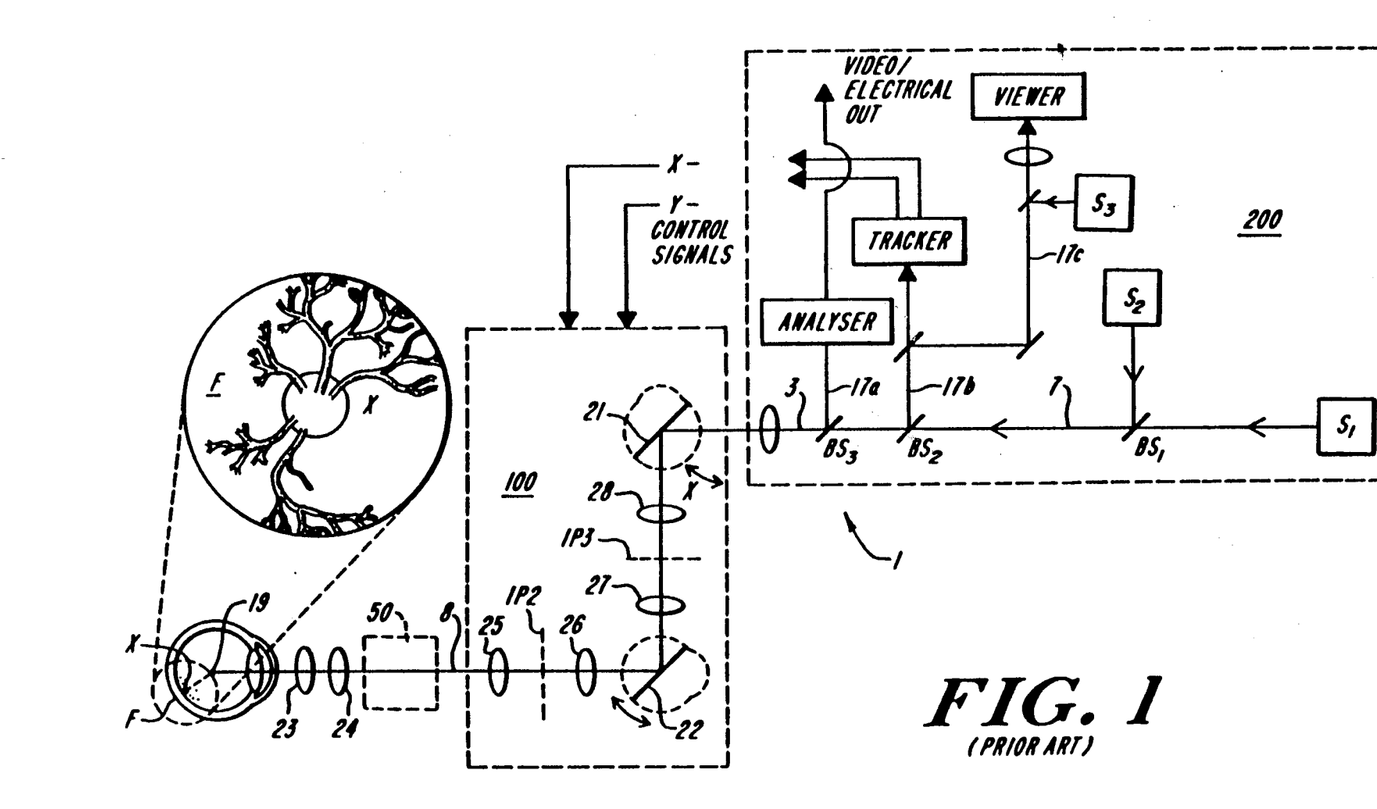
FIG. 1 is a block diagram of an ophthalmic instrument having a bidirectional steering system.

The present invention and the problems it addresses will be best understood by first referring to a prior art instrument employing a bidirectional optical path steering system, and a consideration of its different light signal paths, as illustrated in FIG. 1. FIG. 1 schematically illustrates an instrument 1 for illumination and observing the eye fundus. Instrument 1 includes an instrumentation section 200 having the primary instrumentation for generating illumination and for analyzing or displaying collected reflected light, and a steering section 100 for aiming at the object to be inspected. Section 200 provides illumination from one or more light sources which may, for example, be several laser sources $S_1$, $S_2$ of different wavelengths, and a broadband source $S_3$. A plurality of beamsplitters $BS_1$ and dichroic beamsplitters $BS_2$, $BS_3$ are positioned to direct the light from all the sources along a common optical input path 7 to the steering mechanism 100, and to split off return light passing in the opposite direction along the same general path into a plurality of filtered output beams 17a, 17b, 17c which pass to direct viewing, electrical image forming or analysis, and eye motion image tracking subsystems or the like.

The steering system 100 redirects or steers the optical path 7 to a deviated path 8 by reflection from the surface of x- and y- galvanometer-controlled steering mirror assemblies 21,22, each of which pivots about one orthogonal axis, and is controlled by feedback signals from a tracking system. Such an instrument is described in greater detail in the aforesaid U.S. Patent.

Path 8 leads, via an optional image rotator 50 and objective optics 23,24, to the fundus F of the eye of a subject. The objective optics 23,24, together with various relay lenses 25,26, 27 and 28, are set up such that the eye fundus is imaged in the intermediate planes designated $IP_2$ and $IP_3$ conjugate to the fundus, while the center of rotation 19 of the eye is conjugate to the plane containing the axis of rotation of each mirror 21,22, and is centered on the pivot axis of each mirror.

In the above-described apparatus, all input and output light is reflected from the faces of the two mirrors 21, 22, and the separation of the relatively intense illumination or laser surgical light from the various viewing, treatment or analysis beams is addressed primarily by spectral and spatial light separation techniques. While different, e.g., adjacent, pupils may be set up for different beams, and may be required, for example, for a two-beam Doppler analysis instrument, nonetheless the use of the same mirror surfaces for light traveling in two directions degrades the low-level signals by introducing significant retroreflection and scattering noise.

Figure 2:
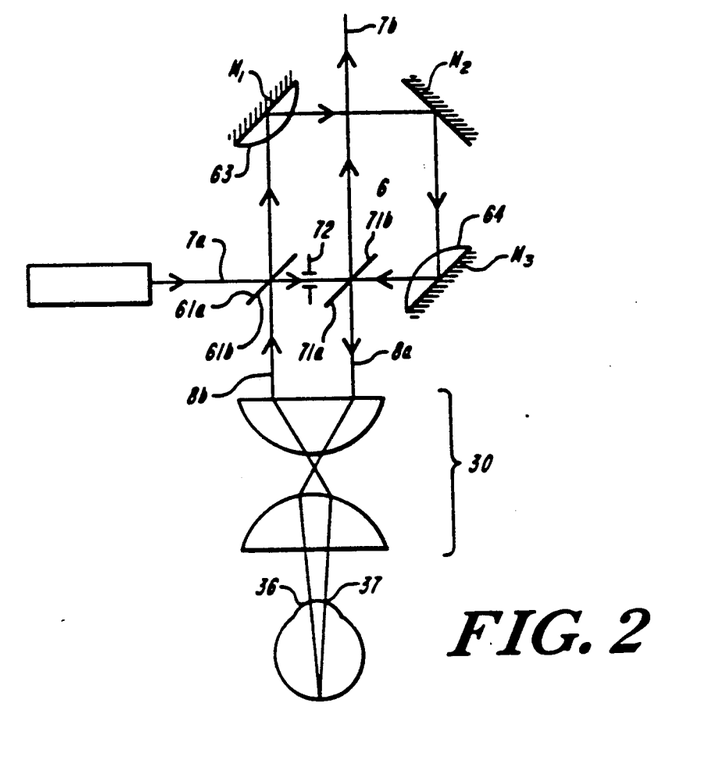
FIG. 2 is a diagram of the improved steering system of the present invention.

These problems are addressed in accordance with the present invention by providing a bidirectional steering system with isometric but disjoint optical paths for the two directions. A basic embodiment of such a steering system 100a according to the present invention is shown in FIG. 2. This system may be substituted for the steering system 100 of FIG. 1 to overcome the above mentioned limitations. System 100a is operative to direct a first light path 7a, illustratively of a laser beam, from x- and y- steering elements 60, 70, respectively, to a deviated or steered output path 8a leading to an objective optical assembly 30, and to receive back along path 8b from the same assembly collected light which is also directed at the first and second steering elements 60, 70 and thereby undergoes an angular transformation closely corresponding to that of input beam 7a, 8a. The steering elements are two sided elements, which are each centered at a pivot axis, and the light paths in opposite directions are reflected from, or are redirected after being incident upon, opposite sides of the elements. Suitable elements are, for example, thin planar mirrors such as a 0.2 mm thick sheet silvered on at least one side and preferably both sides, or possibly specially arranged acousto-optic modulator cells.

For clarity of discussion, these elements, which are operative to redirect light incident upon the element from each of two opposite sides, will be referred to simply as "mirrors" or "two sided mirrors" below. In the case of a conventional mirror, i.e., a sheet of glass with a metallized reflective surface, it is not essential that the two opposite surfaces each be metallized, provided the sheet is sufficiently thin to avoid introducing refractive errors. However, such two-sided reflection coating is preferred to reduce scattering, and for applications in which low-level signal collection is carried out through the steering system, both surfaces are metallized.

In the embodiment shown, the input beam on path 7a is relayed from the outside face 61a of mirror 60 to the outside face 71a of mirror 70 by a fixed arrangement of mirrors M1, M2, M3 which operate as an optical relay to translate path 7a at the central pivot axis of mirror 60 to path 8a at the central pivot axis of mirror 70. As illustrated, mirrors M1, M3 have lens elements 63, 64 on their front surfaces which are telecentric to the pivot axes of the mirrors 60, 70, and thus place the outer sides of the mirrors in conjugate relation. As discussed further below in connection with preferred instrumentation, separate curved mirrors, or lenses located between the planar mirrors are preferably substituted for lenses 63, 64 to reduce scattering and allow greater flexibility in positioning the various components. The optical relay system preferably is of unit magnification, and this property is required for certain stereoscopic instrument embodiments discussed further below.

Continuing with a description of the optical paths in FIG. 2, light reflected from the eye returns through the same objective assembly 30 along a path 8b which strikes the inside face 61b of mirror 60 and is reflected to the inside face 71b of mirror 70, thereby undergoing inverse x- and y- transformations to produce an output beam along an output path 7b which remains stationary as the steering mirrors move.

The inner faces 61b, 71b of the x- and y- steering mirrors are separated by a relatively small distance, which for a one centimeter square galvanometer-actuated mirror may, for example, be under one-half centimeter, so that steering related distortion of the steered beam is minimized without requiring additional precision relay optics to place each inside steering mirror face separately at a conjugate position. When the steering system of FIG. 2 is employed, for example, in a fundus imaging system as shown in FIG. 1, the conjugate pupil plane may be located between the mirrors. In that case, a single artificial pupil 72 positioned between faces 61b, 71b results in spatial filtering of the collected light to obtain both high image quality and high signal collection. In particular, the problem of decentering of the pupil position and the mirror rotation axes is minimized, greatly reducing focal shifts and optical aberrations in the collected image.

In FIG. 2 the input pupil 36, or region of the iris of the eye through which the input light path 8a is directed, and the output or observation pupil 37 through which return light is collected, are each slightly offset from the optical axis of the objective assembly 30, and are conjugate, via assembly 30, with the central pivot axes of the respective mirror faces 71a, 61b. Thus only the second mirror in each path may introduce mechanical scan distortion. This distortion is minimized, in the case of the return imaging path 8b, by the close placement of the mirror inner faces 61b, 71b and the absence of diffractive elements between the faces.

Figure 3:
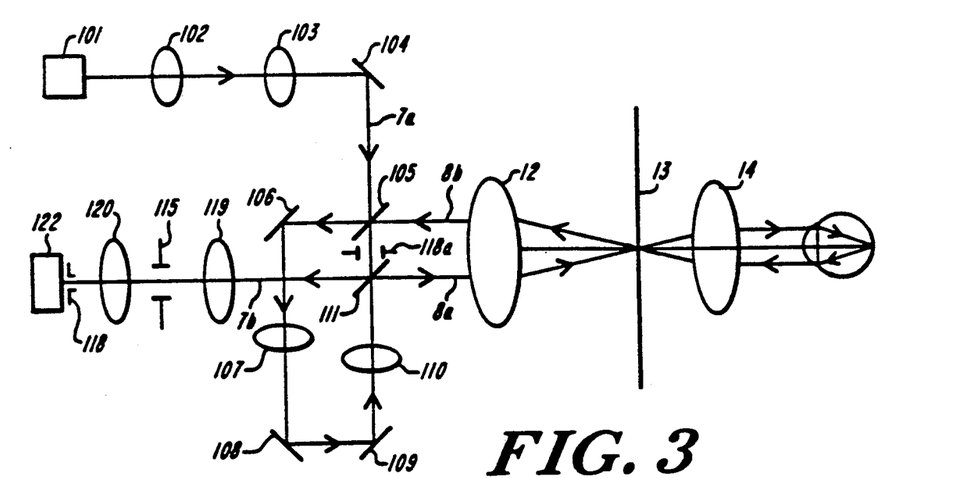
FIG. 3 shows another embodiment of the invention in an imaging instrument.

FIG. 3 shows the system of FIG. 2 with the optical elements 63, 64 replaced by separately mounted lenses 107,110 and with the input light path relocated to the right side for clarity of illustration. Laser 101, optics 102, 103 and turning mirror 104 direct a laser beam at the outer face of one steering mirror 105, and the mirrors 106,108,109 and lenses 107,110 relay the beam to the other steering mirror 110. Objective optics 30 are shown as separate lens assemblies 12, 14 with the front lens 14 forming an image of the eye fundus at plane 13, and the rear lens 12 relaying the image to the mirrors, such that the pupillary plane of the eye lies in the plane of an artificial pupil 118a located between the mirrors. The turning axes of both inside mirror faces, as well as the artificial pupil 118a, thus lie in the plane in which the pupil of the eye is imaged. The lenses 107,110 are adjusted to place the outer faces of the steering mirrors 105,111 in conjugate relation, so that mechanical scan distortion and image decentration are largely avoided.

The image light on path 7b passes by imaging optics 119,120 to an image-receiving unit 122 which, as indicated previously, may be a photodetector, CCD array, camera, reflectometer, doppler analyzer or other imaging or light-analyzing apparatus. A confocal diaphragm 115 conjugate to the fundus plane screens out light from other regions of the eye. A second diaphragm 118 which forms virtual pupil 118a is conjugate, via the optics, to the virtual pupil and to the iris of the eye.

Figure 4:
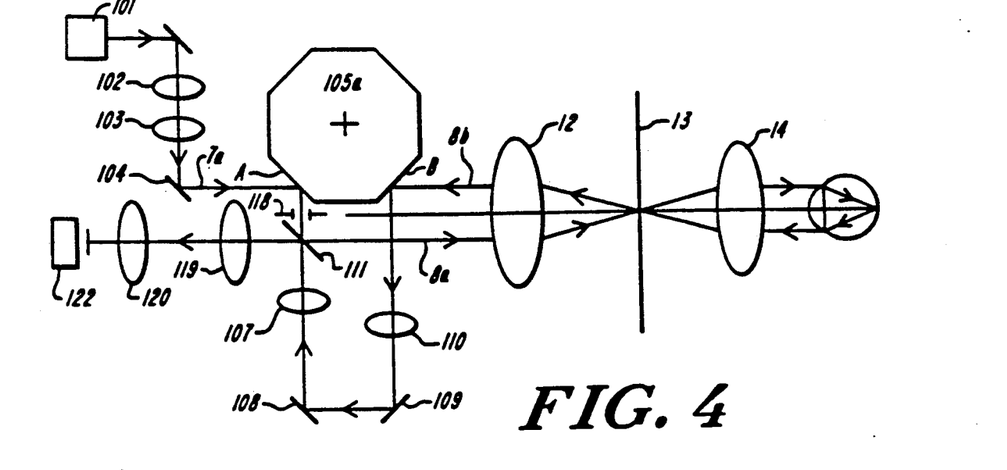
FIG. 4 shows another embodiment of the invention in an imaging instrument.

FIG. 4 shows another embodiment structurally identical to FIG. 3 except that mirror 105 is replaced by a polygon 105a. The input light beam direction is oriented to strike one face "A" of the polygon, and is reflected to the inner face of mirror 111, while the return light strikes a co-rotating face "B" of the polygon which is conjugate, via mirrors 108,109 and lenses 107,110, with the outer face of mirror 111. Such a polygon introduces mechanical scan distortion due to the large translational component of motion, and thus introduces special design constraints and may be suitable only for small angular fields. However, it permits high periodic scanning speeds. In this embodiment, the positions of image analyzer 122 and laser 101 may be interchanged.

Advantageously, the essential symmetry of the input and output paths, and their fixed separation are exploited in one preferred instrument by providing an optical trigger or alternating shutter such as a rotation beamsplitter in a position that is effective to alternately interchange the paths followed by the illumination and the imaging beams.

Figure 5:
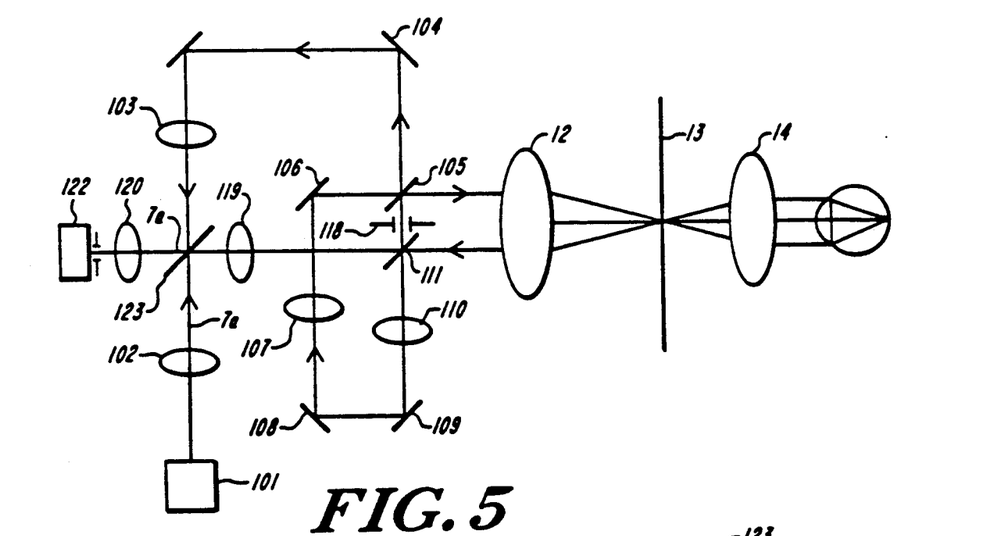
FIG. 5 shows a stereo embodiment of the instrument of FIG. 3 employing a moving beamsplitter.

FIG. 5 shows such a system, with the various elements numbered identically to corresponding elements of FIG. 3. The laser and imaging instrument paths 7a, 7b are oriented such that a rotating beamsplitter 123 either passes illumination along 7a straight through lens 103 whence it is deflected to the outer face of mirror 105, or reflects the illumination from path 7a through lens 119 to the inner face of mirror 111. As the beamsplitter rotates, the inner and outer faces are used alternately to steer the illumination beam from path 7a, while the return beam is steered, by the set of mirror faces not in the illumination path, to the imaging unit 122. One set of directional arrows is drawn in to illustrate the light paths when a reflective sector of rotation beamsplitter is positioned at the junction of paths 7a,7b. By reversing each arrow except the one nearest to the laser and the instrument, the same drawing illustrates the light paths followed when a transmissive sector of rotation beamsplitter 123 is positioned at the path junction.

Figure 5A:
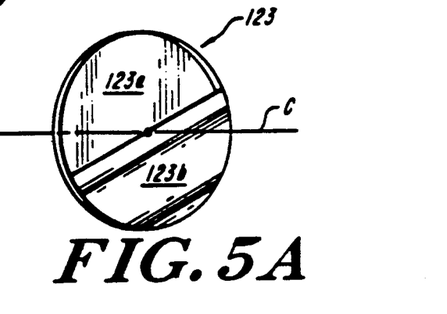
FIG. 5a illustrates one suitable beamsplitter for the instrument of FIG. 5.

FIG. 5a illustrates a typical rotation beamsplitter 123. A thin disc 123 formed of a transparent material is mounted for rotation about a central axis C. One sector 123a of the disc is silvered or otherwise rendered reflective at the wavelengths employed, and another sector 123b is not reflective. Two or more sectors may be provided, depending on the desired sampling or frame rate. The disc is positioned at an angle to the two optical paths 7a, 7b so that as it rotates both paths either proceed through the beamsplitter, or both paths are reflected off the beamsplitter and are redirected.

In order to further reduce the level of noise in a ophthalmic instrument utilizing a steering system in accordance with the invention, the means for translating one steering mirror face to a position conjugate to the other mirror face are realized in a preferred embodiment with a pair of focusing mirror elements rather than the separate planar mirrors 106,108,109 and lenses 107,110 of FIGS. 3 and 5.

Figure 6A:
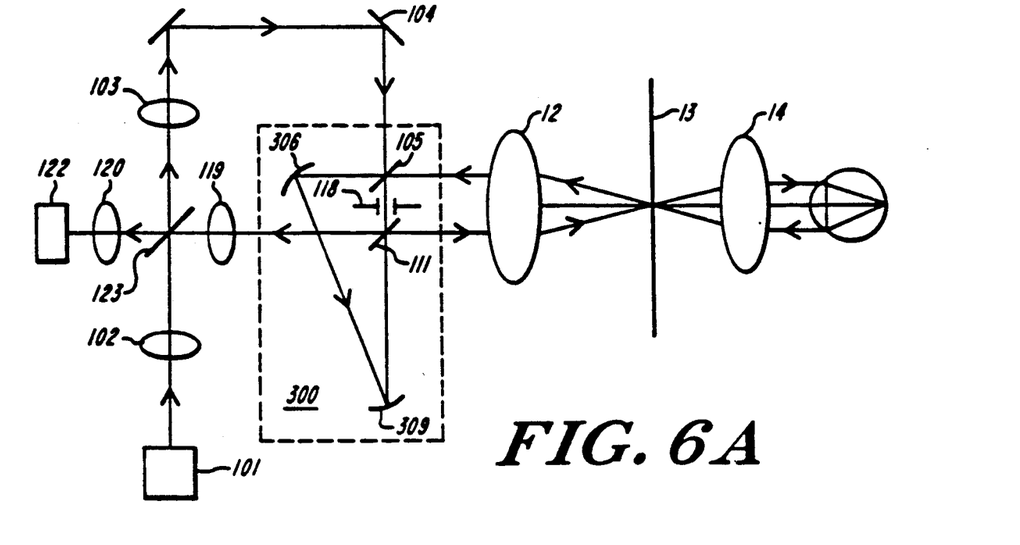
FIGS. 6a and 6b illustrate alternative construction details corresponding to portions of FIGS. 3 and 5.

FIG. 6a illustrates a steering system 300 according to this aspect of the invention. Two curved mirrors 306,309 place the central turning regions of the outer faces of mirrors 105,111 in conjugate relation, thus replacing the three mirrors 106,108,109 and two lenses 107,110. The number of optical surfaces in the conjugation assembly is thus reduced from seven to two, thereby reducing scattering. The use of two reflective elements in this fashion to place the outer faces of the steering mirrors in conjugate positions results in a low noise optical path which is especially suitable for such low light applications as tracking microscopic features at the back of the eye.

In other respects, the embodiment of FIG. 6a is similar to that of FIG. 5. For completeness, the rotation beamsplitter 123 in FIG. 6a is illustrated in a position which passes the light from laser 101 without reflection, so that the illumination and observation light paths are reversed from those of FIG. 5 for all paths between beamsplitter 123 and the eye. In particular the illumination and observation windows in the eye pupil are interchanged, and the relevant faces of each steering mirror are switched.

Figure 6B:
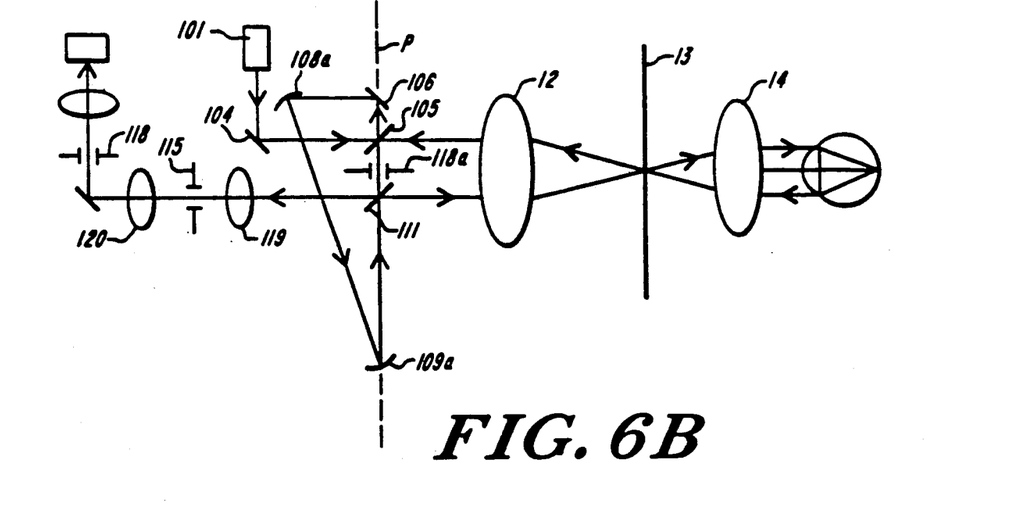

FIG. 6b shows an instrument similar to that of FIG. 3, but having curved mirrors 109a, 108a which operate, together with plane mirror 106 to place the central turning axis at the outer faces of the steering mirrors in a conjugate relation. The pupillary conjugate plane containing the turning axis of both steering mirrors 105, 111, is indicated by P. Aperture 116a also lies in Plane P conjugate to the eye pupil. The relay mirrors 108a, 109a have a curvature to provide unity magnification of the translated beam between mirror 106 and mirror 111, and thus maintain an identity between the input illumination angle and the light collection angle. Conjugate confocal diaphragm 115 filters out light not originating at the retinal plane, so that a CCD, reflectometer or electronic tracking or analysis device may be positioned at any position downstream of diaphragm 115. Alternatively, if diaphragm 115 is omitted, such CCD or the like may be positioned at, or conjugate to, the indicated plane of 115.

The eye objective lenses 12, 14 provide a magnification of approximately 2×, and the steering mirrors 106, 111 effectively act as "virtual" mirrors or apertures positioned in the eye pupil. In order to avoid placing a diaphragm in the small space between these two mirrors, virtual aperture 118a is preferably formed by a physical aperture 118 downstream of and conjugate to 118a.

One useful property of this construction is that the reflective elements lying between lenses 119 and 12 in the Figure may be rotated as a unit around the axis of those lenses without interfering with their function. Thus, when used with an imaging instrument of the type shown in FIG. 1 which has an image rotator to set up and align the field of view, the image rotator 50 need not occupy any space ahead of the steering optics but may constitute or be mounted within the housing of these optical elements.

Figure 7:
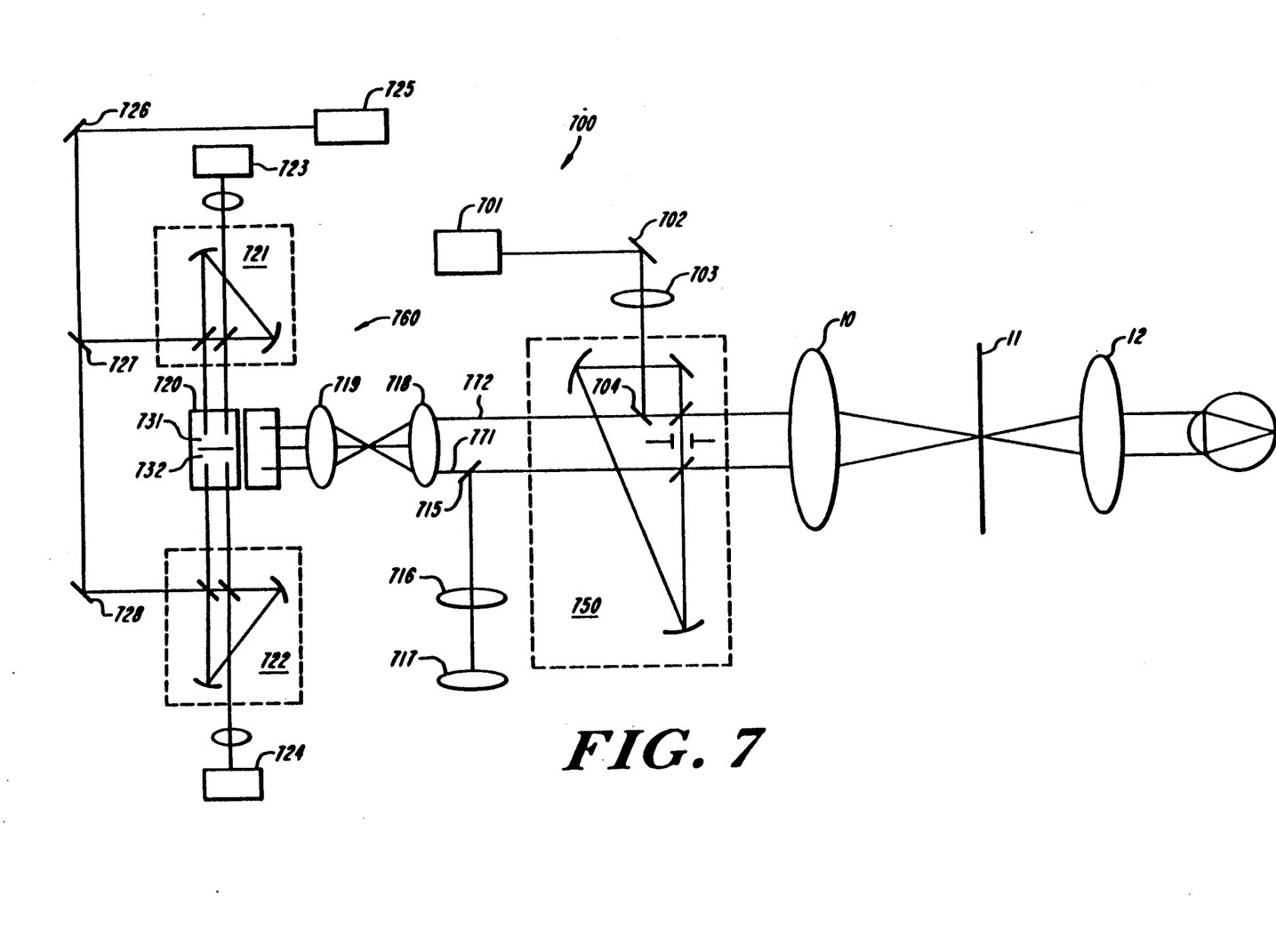
FIG. 7 illustrates a two dimensional tracker instrument embodying the invention.

FIG. 7 shows an instrument 700 for stabilizing a diagnostic beam on the fundus. Instrument 700 operates by tracking the position of two microscopic tissue features on the eye fundus, through an objective steering system which also aims the diagnostic/imaging elements. In this respect, the instrument operates on principals similar to those illustrated in the aforesaid U.S. Pat. No. 4,856,891, wherein separately aligned tracking beams are directed through a common steering system with the instrument's principal beams. The precise structure of the instrument of FIG. 7, however, employs three dual path steering mirror systems together with a separated prism tracking beam element to assure precise alignment and low noise of the many optical paths.

Broadly, instrument 700 employs an eye objective steering assembly 750 through which a diagnostic laser beam is introduced from first laser 701, turning mirror 702 and lens 703 via a dichroic mirror 704 which is reflective at the wavelength of laser 701. A visible return image returns through assembly 750 and is viewed through optics 716,717 via a second dichroic mirror 715. A tracking assembly 760 injects a pair of tracking beams along paths 771,772 which pass through the dichroic mirrors 715,704 respectively, so that the two tracking beams are also steered by the steering assembly 750.

In the tracking assembly 760, a second laser 725 sends a beam of tracking illumination at a different wavelength along a path defined by mirrors 726, 728. A fifty percent reflective mirror 727 directs half the light to a first steering assembly 721, and the remainder of the light passes to a second steering assembly 722. Each assembly 721,722 is identical, except for size, to the assembly 300 of FIG. 6a, and includes a pair of two-sided steering mirror elements and a pair of curved relay mirrors placing the outside faces of the steering mirror elements conjugate to each other.

Each of the two steering assemblies 721,722 is used to steer an input tracking beam which serves as a horizontal tracking beam $a_h$ or a vertical tracking beam $a_v$, respectively, to illuminate a fundus region. Each steering assembly also receives a corresponding return image beam $b_h$ (respectively $b_v$) from the region of the fundus illuminated by its tracking beam. The image beams go to respective detectors 723,724, which may be high resolution CCD arrays as described in the aforesaid U.S. patent.

The four tracking system beams $a_h$, $b_h$, $a_v$, $b_v$ all pass through a prism 720 having offset faces 731,732 which fold the illumination beams into and unfold the imaging beams from a bundle oriented axially with the optics 718,719 and steering system 750, while preserving four separate pupils for the four beams, above and below, and left and right of the principal axis. The prism is a single optical element which serves to define the fixed spacing between the different beams. As further described in the aforesaid U.S. patent, which is incorporated by reference for this purpose, each tracking beam is initially aligned, by manipulating joysticks that control its steering assembly, to illuminate and image a target such as one of a pair of orthogonally oriented microscopic vessels on the fundus. Thereafter, the detector outputs are processed to develop control signals which move the two principal steering mirrors 705,709 of assembly 750 to maintain the two selected target images stationary on detectors 723,724. This automatically also maintains the beam of the diagnostic laser 701, which may, for example be an ablating or coagulating beam, aimed at a fixed spot on the retina.

Thus the instrument of FIG. 7 employs separate x- and y- tracking assemblies, each directed at a separate vessel or other target on the fundus, to provide steering control signals to X- and Y- deflection mirrors 705,709. The diagnostic or imaging light is spectrally separated from the tracking light, and the input illumination paths are separated from the much lower intensity observation paths, thus eliminating a major source of image noise. The prism 720 precisely maintains all four tracking beam paths separate from each other, and allows the paths of laser 701 and observation optics 716, 717 to pass through other separate regions of the eye pupil, further enhancing signal clarity.

In a variation of this structure, the fifty percent reflective mirror 727 may be replaced by a rotation beamsplitter, arranged so that the x- and y- tracking corrections are performed successively, rather than concurrently. The beamsplitter is preferably rotated at a rate to provide several hundred or more steering corrections per second. For example, an imaging rate of one thousand frames per second may be required to maintain a five-micron beam stably positioned for laser surgery.

This completes a description of a bidirectional steering assembly and illustrative instruments employing such assembly for opthalmic imaging in accordance with the present invention. The teachings of the invention being thus disclosed, different variations and modifications will occur to those skilled in the art, and all such variations and modifications are included in the scope of the invention, as defined by the claims appended hereto.

What is claimed is:

1. An optical assembly comprising first and second mirror elements mounted for redirecting light along first and second distinct directions, each said mirror element having a first and a second side each of which is operative to redirect light incident thereon, said mirror elements being positioned such that light traveling along a first path to the first side of the first mirror element is directed to the first side of the second mirror element which directs it along a second path to an objective system, and an optical relay assembly positioned to place the second side of the first mirror element facing the objective system to receive light therefrom, and conjugate to the second side of the second mirror element, so that light collected from the objective system and directed at the second side of the first mirror element is relayed to the second side of the second mirror element and thereby undergoes a corresponding redirection in said first and second directions while maintaining separation of the light traveling along said first and second paths.

2. An optical assembly according to claim 1, further comprising an ophthalmic objective assembly, and wherein each said mirror element moves about a corresponding central turning axis, the turning axes of both mirror elements lying in a plane which is conjugate to the pupil of an eye.

3. An optical assembly according to claim 1, wherein one of the first and the second mirror elements is a thin mirror element.

4. An optical assembly according to claim 1, wherein one of the first and said mirror movable elements is a polygon.

5. An optical assembly according to claim 1, further comprising means for alternately passing illumination light along said first path while receiving observation light along said second path, and passing illumination light along said second path while receiving observation light along said first path.

6. An optical assembly according to claim 5, further comprising imaging means for forming alternating frame images from observation light received along alternate ones of said paths.

7. An optical assembly according to claim 1, wherein the optical relay assembly includes a plurality of fixed mirror elements.

8. An optical assembly according to claim 1, wherein the fixed mirror elements include curved mirror elements.

9. An optical assembly according to claim 1, wherein said optical relay assembly includes an element movable between first and second positions such that in said first position said relay assembly places the first sides in conjugate relation and in said second position said relay assembly places said second sides in conjugate relation.

10. An optical assembly according to claim 1, wherein said objective system focuses at an image plane, and wherein each mirror element has a central turning axis which lies in a conjugate plane thereto, said system having a pupil in said conjugate plane and between said mirror elements.

11. An optical system wherein said pupil is a virtual pupil.

12. An optical assembly according to claim 1, wherein said objective system is directed at a target lying in an image plane, and further including a two dimensional photosensor array located conjugate to said image plane.

13. An opthalmic instrument comprising
a pair of two sided mirror elements having first sides for steering an illumination beam path and second sides for steering an observation beam path,
means placing both of said first or both of said second sides in conjugate relation, and
means for moving each optical path-directing element of said pair to scan in a direction orthogonal to scanning of the other element of said pair, such that when said instrument is positioned in front of an ophthalmic objective assembly to image a region of a patient's eye to which the illumination beam path is directed, return light collected by the objective assembly, and directed along the objective beam path undergoes a steering correction corresponding to that of the illumination path.

14. An opthalmic instrument according to claim 13, wherein said means placing said sides in conjugate relation includes a pair of curved mirrors.

15. An ophtalmic instrument according to claim 13, further comprising
means for forming and positioning tracking beams directed at said first sides, and
means for receiving via said second sides two independent images illuminated by said tracking beams and for analyzing said images to develop control signals therefrom, said control signals being applied to said means for moving to maintain the images stationary.

16. An ophthalmic instrument according to claim 15, wherein said means for forming and positioning tracking beams includes two pairs of two sided mirrors, each mirror of a given pair having one side conjugate to a side of the other mirror of the given pair via an optical relay assembly.

17. An ophthalmic instrument according to claim 15 further comprising stereo camera means for forming stereo images by interchanging the illumination and observation beam paths such that alternate images are formed through two distinct regions of the eye pupil.

18. An optical assembly for steering light along forward and reverse paths to and from an image region, such assembly comprising
first and second mirror elements mounted for movement about orthogonal first and second mirror axes, respectively, each mirror element having an inside and an outside face, the inside faces facing each other,
optical relay means for placing the outside faces conjugate to each other,
the first and second mirror elements being juxtaposed and oriented such that the inside face of the first and the outside face of the second element face in a common direction so that when an illumination beam strikes the outside face of the first element the illumination beam is relayed by the optical relay means to a conjugate position on the outside face of the second element and directed along an output path, and return light arriving adjacent said output path is reflected from the inside face of the first element to the inside face of the second element whereby said return light undergoes a change in direction corresponding to that of the illumination beam.

19. An optical assembly according to claim 18, further comprising a diaphragm stop positioned at or conjugate to a plane intermediate said inside faces.

20. An optical assembly according to claim 18, wherein the optical relay assembly has unit magnification.

* * * * *

UNITED STATES PATENT AND TRADEMARK OFFICE
CERTIFICATE OF CORRECTION

PATENT NO. : 5,094,523
DATED : March 10, 1992
INVENTOR(S) : Yakov Reznichenko; Michael T. Milbocker It is certified that error appears in the above-identified patent and that said Letters Patent is hereby corrected as shown below:

Column 9,
Line 41, delete "system" and insert therefor --assembly according to claim 10--.
Line 48, delete "opthalmic" and insert therefor --ophthalmic--.

Column 10,
Line 5, delete "opthalmic" and insert therefor --ophthalmic--.
Line 8, delete "ophtalmic" and insert therefor --ophthalmic--.

Signed and Sealed this

Twenty-sixth Day of June, 2001

*Attest:*

NICHOLAS P. GODICI
*Attesting Officer*     Acting Director of the United States Patent and Trademark Office